United States Patent
Wien

(10) Patent No.: US 6,537,257 B1
(45) Date of Patent: Mar. 25, 2003

(54) SYRINGE WITH RECIPROCATING, LEAK-PROOF NEEDLE GUARD

(76) Inventor: Abraham Wien, 11990 SW. 94th Ct., Miami, FL (US) 33176

( * ) Notice: Subject to any disclaimer, the term of this patent is extended or adjusted under 35 U.S.C. 154(b) by 0 days.

(21) Appl. No.: 09/432,380

(22) Filed: Nov. 1, 1999

(51) Int. Cl.⁷ ................................................ A61M 5/32
(52) U.S. Cl. ...................................................... 604/198
(58) Field of Search ................................ 604/192–201, 604/263, 187, 110

(56) References Cited

U.S. PATENT DOCUMENTS

| | | | | |
|---|---|---|---|---|
| 5,591,138 A | * | 1/1997 | Vaillancourt | 604/263 |
| 5,855,839 A | * | 1/1999 | Brunel | 264/524 |
| 5,971,181 A | * | 10/1999 | Niedospial, Jr. et al. | 215/247 |

* cited by examiner

*Primary Examiner*—Anhtuan T. Nguyen
*Assistant Examiner*—Ann Y Lam
(74) *Attorney, Agent, or Firm*—John H. Faro

(57) ABSTRACT

A leak proof safety shield/guard for a syringe is herein disclosed. The shield/guard provides for not only protection of the syringe from a damage and abuse in the storage and handling, but also protects the health care professional from contact with the used needle and any of the tissues or fluids adherent thereto. Moreover, any and all fluids that are initially contained within the syringe, or subsequently collected from a patient, are also isolated from inadvertent discharge or loss. This device achieves such objectives by providing a sealed protective guard that retains its integrity subsequent to use of the syringe. Additional enhancements to the device of this invention include a locking mechanism that prevents re-use of the syringe; and, additionally causes the syringe to be rendered physically inoperative.

4 Claims, 2 Drawing Sheets

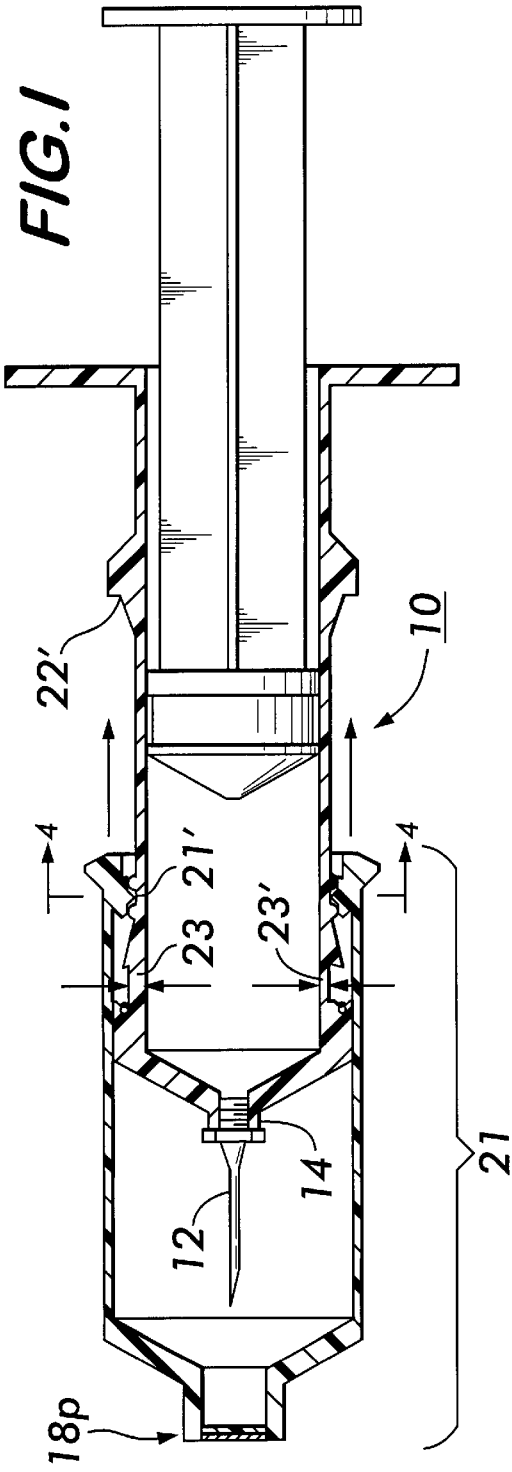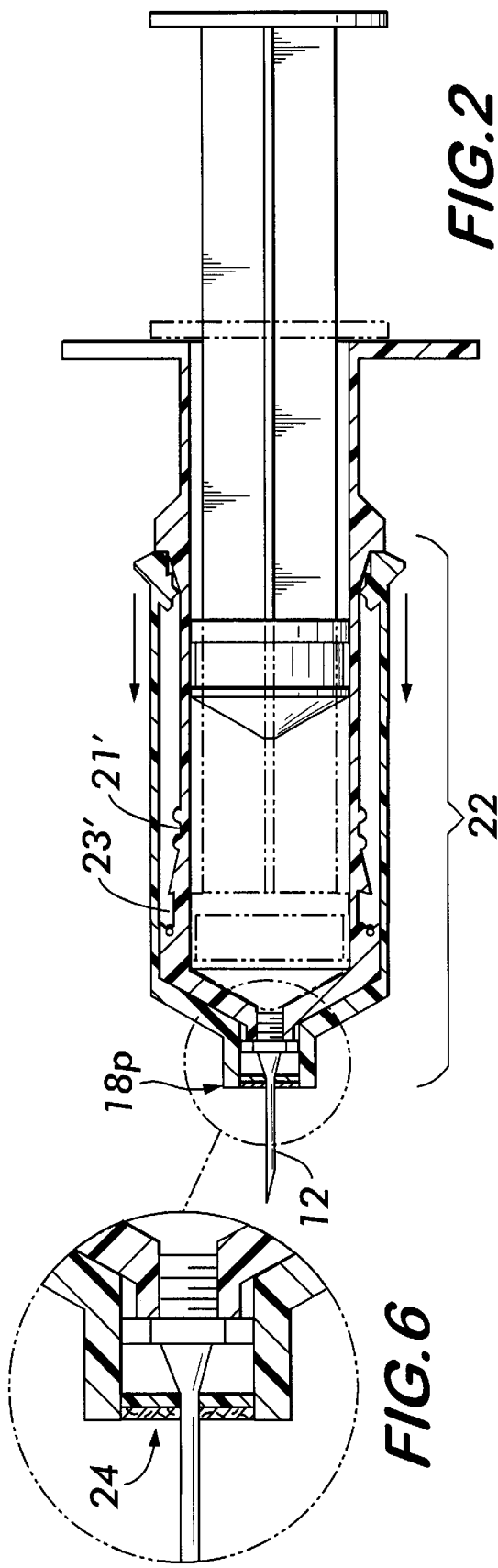

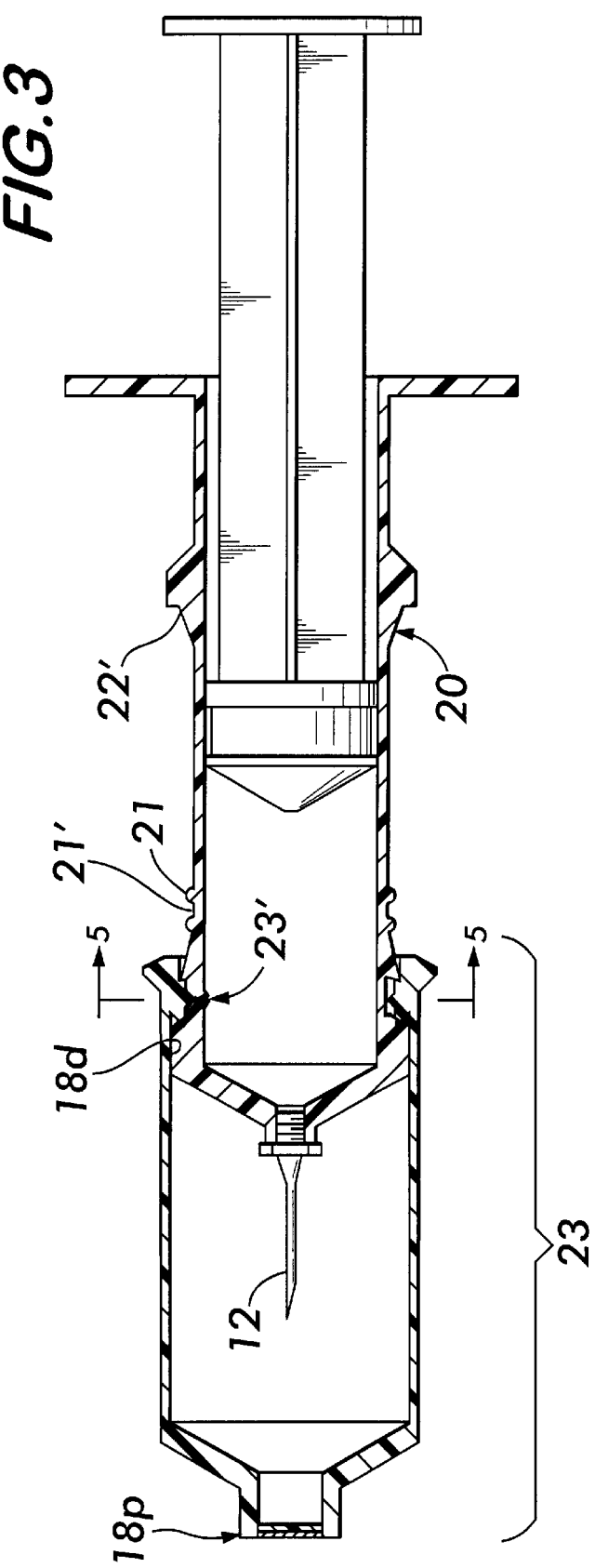
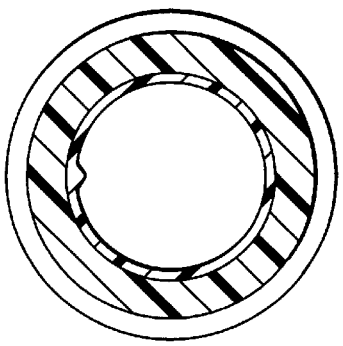
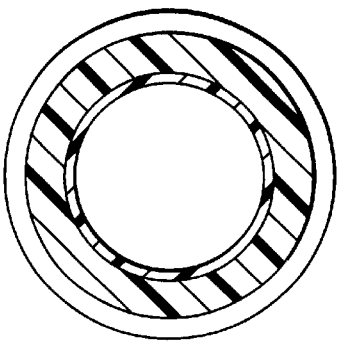

SYRINGE WITH RECIPROCATING, LEAK-PROOF NEEDLE GUARD

BACKGROUND OF THE INVENTION

1. Field of the Invention

This invention relates to a device and to method. More specifically, this invention relates to a medical device, in the form an improved syringe for dispensing or, alternatively, collecting of potentially infectious biological fluids; and, to the method for the isolating such fluids within the collection device.

2. Description of the Prior Art

The prior art is replete with various contrivances for use in combination with a syringe/needle to both protect and isolate the needle, both before and after use, so as to prevent inadvertent injury to a clinician or phlebotomist. In addition, the illicit and multiple use of a syringe/needle has also been the subject of intense focus because of the prospect of transfer of infectious diseases. In each instance, the expedient suggested has been, with minor variation, essentially the same. The needle is initially isolated from the ambient environment prior to use, and subsequent to use, the needle and/or the barrel of the syringe rendered inoperative (preferably without exposure to the collected fluid or to the injury from the used needle). The following patents are representative of the relevant prior art and, are therefore discussed herein. The following patents are discussed in chronological order of their date of issue and, thus, no significance is to be attached to the order of their discussion.

U.S. Pat. No. 2,704,073 (to Jensen, issued Sep. 21, 1953) describes a unique solution dispensing device in the nature of an ampoule or vial having a conventional end (e.g. septum closure for access of medicant fluid contents) and a reciprocating syringe-like piston assembly fitted into the based of the solution container. This piston is connected to an internally mounted needle which is contained within the vial/ampoule. Upon exertion of pressure on the plunger, the needle is advanced a short distance within the vial until it penetrates the septum (from within the vial). It is then available for placement at the dispensing/administration site. Upon insertion of the needle into the patient, the plunger is then advanced further. The further advancement of the plunger, allows for the contents of the vial to be drawn/forced through a hole in the needle shaft and thereby delivered/dispensed fluid from the exposed end thereof. The continued advancement of the plunger within the vial forces the contents from the vial and through the needle. The obvious disadvantage of this system is that the needle also continues to move relative to and in response to the pressure on the plunger, and thus may inadvertently extend beyond the desired depth of tissue penetration or possibly puncture a blood vessel. Moreover, the design adopted by patentee is apparently only useful in the dispensing of the contents of the vial, as opposed to sample collection, because the position of needle changes in the course of movement of the plunger/ram, as does the accessibility of the fluid channel through the needle into the container.

U.S. Pat. No. 5,002,533 (to Jullien—issued Mar. 26, 1991)—describes a needle guard for use with a hypodermic syringe. The needle guard comprises a retractable tubular member that fits over the syringe barrel. The end of the guard is provided with an end-piece that permits, alternate, opening and closing of an aperture at the end of the guard so as to allow the syringe needle to pass through the aperture in the end of the guard upon the retraction of the guard over the syringe barrel. In one of the embodiments of the Jullien device, the end piece is repositioned over the aperture at the end of the guard upon the extension thereof over the needle. The needle is once again forced forward and into the end-piece and thereby blunted, bent or otherwise rendered inoperative so as to prevent its re-use.

U.S. Pat. No. 5,057,087 (to Harmon—issued Oct. 15, 1991) describes a hypodermic needle safety system in which the exposed needle is protected by a removable protective cap. The removable cap is held in place by friction fitting thereof to the end of an axially movable safety sleeve. In use, the cap is removed and the safety sleeve retracted and locked in place on the syringe barrel. Upon conclusion of use of the syringe, the safety sleeve is extended to once again surround the needle. The extent of extension of the safety sleeve is somewhat more advanced than its initial position prior to use to allow for the coupling/locking engagement thereof to the end of the syringe barrel upon its reinstallation. More specifically, the additional extension/advancement of the safety sleeve causes one or more détentes within the protective sleeve to engage and lock the movable safety sleeve onto the syringe barrel upon its insertion of the sleeve. Thus, the syringe can no longer be re-used, while once again protecting one from exposure to injury and transmission of disease.

In one of the alternative embodiments of the Harnon device a sealant/adhesive is disposed at the interface of the guard and the syringe barrel to effect sealing of the guard to prevent inadvertent discharge of fluids from the syringe.

U.S. Pat. No. 5,125,908 (to Cohen—issued Jun. 30, 1992)—describes a hypodermic syringe with a protective holder. The protective holder comprises a tubular structure fitted to the barrel of a syringe. The syringe operates by dispensing fluids from a needle that extends through an aperture in the end of the protective holder. A rubber plug is fitted onto the end of the needle to protect it from damage during the assembly of the syringe and protective holder. Prior to use, the protective holder is retracted to permit advancement of the needle through the aperture at the end of the holder. In the course of advancement of the needle, the needle penetrates the rubber plug that is displaced relative to the needle tip. The contents of the syringe are then dispensed in the traditional manner. Upon completion of the use thereof, the protective holder is re-positioned over the needle from its retracted position to it original protective position; and, the aperture at the end thereof capped as before. Upon retraction of the needle, the rubber plug is not re-positioned over the end of the needle but rather remains remote from the tip of the needle and the aperture in the end of the protective holder.

U.S. Pat. No. 5,139,490 (to Vetter et al—issued Aug. 18, 1992) describes a hypodermic syringe that is typically pre-filled with a medicinal solution (e.g. insulin). The syringe barrel is capped on the dispensing end thereof with a rubber/elastomer seal; and, is fitted on the opposite end of the syringe barrel with a plunger. Prior to use, a needle is fitted to the dispensing end of the barrel. The needle is double ended and, upon mounting to the syringe, pieces the rubber/elastomer seal with one (the distal) end thereof. The act of mounting of the needle on the syringe barrel, thus, causes the distal end of the needle to puncture the seal on the dispensing end of the syringe barrel and thereby permits the plunger to dispense the contents of the syringe through the needle. Presumably the needle can then be removed and the fluid contents remaining within the syringe resealed for use at a later time. Vetter does not disclose how he disposes of the used needle, and presumably it is not reused but rather discarded in the conventional manner.

U.S. Pat. No. 5,647,849 (to Kalin issued Jul. 15, 1997) describes a self-contained safety syringe similar in concept to the device discussed herein relative to U.S. Pat. No. 5,057,087 (to Harmon). The Kalin device is provided with a safety shield that is slidably mounted on a syringe barrel. The open end of this safety shield is covered with a removable cap (and presumably discarded). When it is time to use the syringe, the cap is pealed off the end of the safety shield and the safety shield retracted over the barrel. In one of the alternative embodiments of this invention, the cap is not separately removed, rather the needle simple punctures this shield upon relative movement of the shield and the needle, as the shield is retracted over the barrel, Summary of the Invention, Col. 3, lines 22–26. There is no drawing specifically illustrating this alternative and it is assumed that the FIGS. (and their respective descriptions) that are included are inclusive of this alternative.

Each of the opposing surfaces of the safety shield and the syringe barrel are provided with a series of detentes for releasable engaging the shield relative to the barrel. Thus, once the syringe has been used, the shield is disengaged from its retracted position on the syringe barrel and once again extended so as to re-position it over the exposed needle.

As is evident from the foregoing the abbreviated review and discussion of the prior art, a number of inventions have endeavored to provide a shield or guard to protect syringe users from injury and disease, by physical isolation of a hypodermic needle within a retractable (e.g. reciprocating) or removable shield. In each instance, the shield or guard is configured to provide a physical barrier to prevent inadvertent contact (and possible puncture) with the needle. Notwithstanding such features, none of the known devices provide effective protection from unintended exposure to the contents of the syringe in the event of leakage or inadvertent discharge of the contents of syringe from the needle. A possible exception to the above, is the device described by Harmon (U.S. Pat. No. 5,007,087) where redeployment of the Harmon shield causes dispensing of an adhesive at the interface of the guard and the syringe barrel and thereby glue the two components to one another. This latter configuration, however, is still not generally leak-proof. Thus, there continues to exist deficiencies in the prior art devices as to the provision of a fluid collection syringe configuration that can prevent inadvertent discharge/spilling of fluid from the syringe (the latter being of significance where the contents of the syringe contain an infectious sample or a solution containing a radioactive isotope.

OBJECTS OF THE INVENTION

It is the object of this invention to remedy the above as well as related deficiencies in the prior art.

More specifically, it is the principle object of this invention to provide a medical device that is both safe and effective for the collection and/or dispensing of fluids, and the containment of such fluid within the device, so as to prevent inadvertent discharge.

It is another object of this invention to provide a disposable (single use) syringe/needle combination having an axially movable, reciprocating guard to protect the needle prior to use, retracts during use and, thereafter, upon redeployment, seals the needle within a fluid tight environment.

It is yet another object of this invention to provide a disposable (single use) syringe/needle combination having an axially movable, reciprocating guard to protect the needle prior to use, retracts during use and, thereafter, upon redeployment, concurrently renders the syringe inoperative, and minimize inadvertent discharge of fluid.

Additional objects of his invention include the provision of a method for the protection of an individual from injury and/or infection by the effective sealing of a needle and the fluid contents of a syringe with a leak-proof guard disposed on the dispensing/collection end of the syringe.

SUMMARY OF THE INVENTION

The above and related objects are achieved by providing a single use, disposable syringe/needle combination wherein an axially movable, reciprocating shield or guard is slideably mounted over the barrel on the dispensing/collection end of the syringe to protect and shield the needle from contamination prior to use, retracts to permit accessibility of the needle for dispensing and/or collection of fluid through the needle, and, thereafter, subsequent to use, redeployment of the guard, to effectively isolates and seals the needle in a fluid tight chamber, so as to prevent any residual fluid or tissue that may be present thereon, from contact with a health care professional or the environment of the health care professional. This axially movable, reciprocating guard is preferably tubular, of a regular or essentially uniform inside diameter, and has an open, or distal end, and a closed, or proximal end. The inside diameter of the guard is of essentially the same dimension as the outside diameter of the syringe barrel and slidingly mounted on the barrel, at the distal end thereof, by means of one of more features/elements which are complimentary to features/elements on the barrel. This distal end of the guard is further provided with means for engagement of the barrel, on at least three (3) distinct positions, depending the life/use cycle of the device:

at time of shipment—to protect the needle from contamination in shipment and prior to use, at time of collection or dispensing of fluid through needle—in a retracted position to permit accessibility of the needle for collection or dispensing fluid relative to the syringe barrel and, at time of disposal—subsequent to use and upon re-deployment, to seal the needle in a fluid tight compartment.

It is emphasized that the relative position of the guard on the syringe barrel is, in each instance, determined by the placement of a complimentary and engaging feature which is preferably molded into the outer surface of the syringe barrel.

In one of the alternative embodiments of this invention, the redeployment of the guard extends the proximal end thereof beyond its original (shipment) position relative to the syringe barrel so as to engage an element on the barrel and thereby cause such element to penetrate through the barrel and thereby render the syringe permanently inoperative. In a preferred embodiment of this alternative configuration, this element (which can be attached to either the guard or the syringe barrel) is movable or hinged so that upon extension of the guard to its outermost position (and the relative movement of such locking element vis-a-vis the syringe barrel), the guard exerts pressure on such element and causes such element to pierce the syringe barrel, thereby rendering it useless. It is important to emphasize that notwithstanding the damage caused to the syringe barrel, any residual fluids that may remain within the syringe are confined within the leak proof guard.

As is evident from the following description and accompanying Figures, the overall length of the guard is somewhat longer that the needle and terminated on the proximal end thereof with a self-sealing, preferably elastomeric, membrane or septum, such as that typically used on a vial or other container commonly used to store sterile solutions. The location/position of the self-sealing membrane or septum is coincident with the projected path of the needle through the proximal end of the guard. Upon axially movement of the guard, the needle is urged forward and through this self-sealing membrane or septum. Upon emergence of the needle from the sealed environment of the guard, through the self-sealing membrane or septum, the syringe can be used in the conventional manner to collect a biological fluid sample, or dispense a fluid (e.g. insulin solution) contained therein.

Upon retraction of the guard, it is unobtrusively secured in place, on the syringe barrel by means of one or more surface or detente features that releasably engage the interior surface of the guard and with a complimentary feature on the surface of the syringe barrel. The engagement of the guard and syringe barrel can be effected by simply making the syringe barrel irregular or of a larger diameter at the proximal end thereof.

Upon completion of the sample collection, or alternatively, the medicant dispensing cycle, the needle is withdrawn from the patient, and the syringe contents are secured. This is achieved by a combination of processes which can include the physical separation of, for example, a Vacutainer-like vessel from the syringe barrel, or alternatively, the dispensing of an aliquot of the sample into a separate container/sample tubes for further analysis/storage, or alternatively, the dispensing of an aliquot of the sample into the fluid tight guard and thereafter separation of the guard and needle from the syringe barrel.

The re-deployment of the guard secures the needle within a sealed and protected environment. As above noted, such redeployment of the guard subsequent to use, can also concurrently render the syringe barrel and/or plunger inoperative by forcing a piercing element through the wall of the syringe barrel incident to locking the guard in place for safe disposal of the syringe.

BRIEF DESCRIPTION OF THE DRAWINGS

FIG. 1 is a longitudinal, cross-sectional view of one of the preferred embodiments of the device of this invention, as it would appear at the time of shipment from the manufacturer.

FIG. 2 is a longitudinal, cross-sectional view of one of the preferred embodiments of the device of this invention, as it would appear at the time of collection or dispensing of fluid through the needle of the device.

FIG. 3 is a longitudinal, cross-sectional view of one of the preferred embodiments of the device of this invention, as it would appear subsequent to use and prior to disposal.

FIG. 4 is a cross-sectional view through the device depicted in FIG. 1

FIG. 5 is a cross-sectional view through the device depicted in FIG. 3

FIG. 6 is an enlarged view in of a composite septum of the device of FIG. 2.

DETAILED DESCRIPTION OF THE INVENTION INCLUDING PREFERRED EMBODIMENTS

The Figures that are described hereinafter have one or more components in common, and thus many of their features are assigned a common reference numeral for ease of understanding and continuity of expression.

FIG. 1 illustrates the fluid collection/dispensing device (10) of this invention, as it is shipped from the manufacturer. In this configuration, the needle (12) is attached to a cannula fitting (14) on the end of a syringe barrel (16). The needle is confined within a needle guard (18) that is axially movable relative to the syringe barrel (20). The syringe barrel (20) is further provided with a number of surface features (21, 22, 23) on the exterior surface thereof to engage the needle guard (18) at anyone of three different positions (21', 22', 23'), dependant upon the stage of usage of the device. In FIG. 1, the guard (18) is positioned at an extended position (21') relative to the needle (12) so as to afford physical protection and isolation thereof.

In the improved device of this invention, the needle guard (18) can be repositioned along the syringe barrel (20), as appropriate, depending upon the stage of us of the device. Each of the three points of engagement (21', 22', 23') of the needle guard (18) with the surface features of the syringe barrel (20) corresponds with a different needle position, and, different stages of use of the collection device. Each such point of engagement is represented by a ramp/detente along the surface of the syringe barrel, and further characterized by its size/shape relative to the complimentary feature on the interior wall of the guard. Locking the guard on the barrel at any one of these positions may be achieved by a simple linear movement of the safety shield relative to the syringe barrel, for example, as described in U.S. Pat. Nos. 5,342,309 and 5,3857,555, both of which are herein incorporated by reference. Alternatively, the locking structure may require a combination of linear and rotational movement to achieve the permanent locking of the safety shield in the distal after-use position, for example, as described in U.S. Pat. No. 5,403,287, which is also herein incorporated by reference.

The subject invention includes substantial enhancements to the prior art by provision of a fluid tight guard (18) to contain and protect the needle (12) in shipment and, thereafter, isolate both the needle and any residual contents of the syringe from inadvertent contact/exposure to the health care professional or the environment. The device in these Figures provides these enhancements by utilization of a permanent, elastomeric seal or septum (24), as an integral component of the proximal end (18p) of the needle guard (18). The guard (18), as shown in FIG. 1, is in the original or extended position (21') relative to the needle (12) to insure protection of the needle (12) from contamination in shipment/storage, prior to use.

The proximal end of the guard (18p) is provided with an integral, pieceable, self-sealing septum (24) that affords a fluid tight seal both prior to use and upon re-deployment of the guard (18) incident to the disposal of the syringe subsequent to use. In each instance, the simple axial and reciprocating movement of the guard (18), in the direction indicated by the arrows, engages the barrel, as appropriate, and thereby positions the guard (18) at the proper attitude relative to the needle (12). For example, FIG. 2 depicts the guard (18) in the retracted position relative to the needle (12). In the retracted position (22'), the needle (12) is projected through the septum (24) and, thus, accessible for collection and/or dispensing fluids relative to the syringe. The guard (18) is maintained in the retracted position (22') by engagement thereof with surface features (22) on the syringe barrel. The surface feature (22) simple comprises an enlargement of the syringe barrel (20) at the point of engagement of the interior surface of the guard (18). It is noted that such engagement provides for releasable coupling of these two components to permit re-deployment of the guard (18) upon conclusion of the collection or dispensing fluids through the needle.

Subsequent to use, the guard is disengaged and re-deployed, as shown in FIG. 3. More specifically, the guard (18) is disengaged from its retracted position (22') and extended to its outmost position (23') (advance beyond the original position) so as to engage and lock the guard and thereby immobilize it on the end of the sample collection device. This locking engagement of the guard with the outermost complimentary features (23) on the end of the syringe barrel, cannot be undone. Accordingly, the guard (18) is no longer axially movable and, thus, the resultant device cannot be made to function as before. The interior surface of the distal end of the needle guard (18d) is finished (e.g. ground glass-like finish) to provide an effective fluid tight seal with the syringe barrel at the point of engagement thereof.

As the guard (18) is re-deployed, the needle (12) is once again totally isolated from contact with surrounding environment. It is possible, in a limited number of instances, that the needle (12) may contain residual fluid or tissue on its surface or at its tip. Thus, upon retraction, such residual materials may be transferred to the septum (24) as needle is withdrawn through the septum. In order to further insure against inadvertent exposure to such residual materials, the septum (24) can be modified by lamination of porous, adsorbent film to its exterior surface. The resultant composite retains the self-sealing characteristics of the septum and yet provides the additional protection of a blotter. This absorbent medium can be a separate layer or integral with the septum. Typical of such materials suitable for this function include an open cell foam or a sheet of blotter like material.

In extreme cases of abuse, the guard can broken and removed so as to once again expose the needle and permits its re-use, (e.g. multiple use of syringes by intravenous drug users). In order to prevent such re-use from occurring, an alternative embodiment of the device (10) of this invention provides an articulating element (23) associated with the guard (18) that is engaged by the guard (18) as it is advanced and locked in place on the end of the syringe barrel (20). This element is either preferably integral with the syringe barrel or with the guard, and upon re-deployment and locking of the guard, is forced by the guard to penetrate through the surface of the syringe barrel and puncture the barrel. This piecing of the syringe barrel, illustrated in cross-section of the device in FIG. 5, effectively destroys the syringe by prevention of re-filing or further dispensing of fluid from the syringe barrel.

Additional enhancements to the device of this invention include the addition of other common and complimentary accessories known in the art.

What is claimed is:

1. The assembly having a self-contained syringe comprising a barrel equipped with a plunger, a hypodermic needle affixed to one end thereof and a shield or a guard slidable mounted on said barrel and in reciprocating relation to said needle, whereby said shield or guard can be slidable retracted and/or extended relative to said barrel to shield said needle from exposure or contact prior to use thereof and, upon removal or retraction of said shield, permit said needle to project from the end of said assembly and to allow for collection or dispensing of a fluid through said needle relative to the barrel of said syringe, the improvement comprising:

a slidable, barrel mounted, reciprocating shield in the form of a fluid tight container for isolation of a syringe needle mounted on a syringe, having
 A. an open end characterized by an essentially fluid tight seal for mating engagement with a barrel of a syringe, said seal being further characterized as permitting both reciprocating movement, upon retraction of said shield relative to along said barrel of said syringe, and sealing of said needle and fluid within said shield, upon re-deployment of said shield beyond the end of said needle, and
 B. a closed end having a resealable permanent elastomeric seal integral with said shield and disposed in-line with said syringe needle, whereby upon relative axial movement of said shield along said barrel, said needle penetrates said septum and, upon extension of said shield relative to said barrel, reseals said needle within said shield, whereby, and fluids that are disposed within said barrel and inadvertently discharged through said needle are retained within said shield.

2. The improvement of claim 1, wherein said shield is further provided with a series of surface features which interlock with features on said barrel in at least three distinct positions along said barrel, so as (a) to retain said shield in a first extended position to protect the needle from contamination in shipment and prior to use, (b) to retain said shield in a retracted position during the collection and/or dispensing through said needle relative to said barrel and (c) to retain the shield in a second extended position and thereby engage means on said barrel so as to a cause said means to penetrate said barrel and thereby render said syringe inoperative.

3. The improvement of claim 1, wherein said resealable septum comprises a composite with includes a layer of an elastomeric material and a layer of a fluid absorbing material.

4. A method for prevention of inadvertent fluid discharge from a syringe and the containment thereof, if and when inadvertently discharged, within a leak-proof needle guard disposed on the end of the syringe, said method comprising:
 A. providing a slidable, barrel mounted, reciprocating shield in the form of a fluid tight container for isolation of a syringe needle mounted on a syringe, said shield being characterized as having
  (1) an open end which includes an essentially fluid tight seal for mating engagement with a barrel of a syringe, said seal being further characterized as permitting both reciprocating movement, upon retraction of said shield relative to along said barrel of said syringe, and sealing of said needle and fluid within said shield, upon re-deployment of said shield beyond the end of said needle, and
  (2) a closed end having a resealable permanent elastomeric seal integral with said shield and disposed in-line with said syringe needle, whereby upon relative axial movement of said shield along said barrel, said needle penetrates said septum and, upon extension of said shield relative to said barrel, reseals said needle within said shield, whereby, and fluids that are disposed within said barrel and inadvertently discharged through said needle are retained within said shield.

* * * * *